(12) United States Patent
Shih et al.

(10) Patent No.: US 8,507,446 B2
(45) Date of Patent: Aug. 13, 2013

(54) USE OF PEDF-DERIVED POLYPEPTIDES FOR TREATING LIVER CIRRHOSIS

(75) Inventors: Shou-Chuan Shih, Taipei (TW); Yeou-Ping Tsao, Taipei (TW); Tsung-Chuan Ho, Taipei (TW)

(73) Assignee: MacKay Memorial Hospital, Zhongshan District, Taipei (TW)

( * ) Notice: Subject to any disclaimer, the term of this patent is extended or adjusted under 35 U.S.C. 154(b) by 0 days.

(21) Appl. No.: 13/206,238

(22) Filed: Aug. 9, 2011

(65) Prior Publication Data
US 2013/0040899 A1 Feb. 14, 2013

(51) Int. Cl.
*A61K 38/16* (2006.01)
*A61K 38/17* (2006.01)
*A61K 38/18* (2006.01)

(52) U.S. Cl.
USPC .......................................... 514/21.3; 514/7.6

(58) Field of Classification Search
None
See application file for complete search history.

(56) References Cited

U.S. PATENT DOCUMENTS

| | | | | |
|---|---|---|---|---|
| 5,194,596 | A | * | 3/1993 | Tischer et al. ............... 530/399 |
| 5,350,836 | A | * | 9/1994 | Kopchick et al. ............ 530/399 |
| 6,451,763 | B1 | * | 9/2002 | Tombran-Tink et al. ...... 514/8.4 |

OTHER PUBLICATIONS

Benjamin et al., 1998, Development 125:1591-1598.*
Vukicevic et al., 1996, PNAS USA 93:9021-9026.*
Shen et al., 2004, Eur. J. Neurosci. 20:2031-2037.*
Massague, 1987, Cell 49:437-8.*
Pilbeam et al., 1993, Bone 14:717-720.*
Tsung-Chuan Ho et al., "Pigment Epithelium-Derived Factor is an Intrinsic Antifibrosis Factor . . . ", The American Journal of Pathology, vol. 177, No. 4, Oct. 2010, p. 1798-1811.
Xiao et al. " Production of High-Titer Recombinant Adeno-Associated Virus Vectors in the Absence of Helper Adenovirus", Journal of Virology, Mar. 1998, p. 2224-2232.
Yeou-Ping Tsao et al. "Pigment epithelium-derived factor inhibits oxidative stress-induced cell death by activation of extracellular . . . " Life Sciences 79 (2006) 545-550.
Esther Titos, et al. "Inhibition of 5-lipoxygenase induces cell growth arrest . . . " The FASEB Journal express article 10.1096/fj.02-1157fje. Published online Jul. 3, 2003.
Yongseok Kim et al."Transcriptional Activation of Transforming Growth Factor . . . "The Journal of Biological Chemistry, vol. 273, No. 50, Issue of Dec. 11, pp. 33750-33758, 1998.
M. Behnan Sahin et al., "Isolation and Characterization of a Novel Population . . . " Liver Transplantation 14:333-345, 2008.
Takeo Miyahara, et al., "Peroxisome Proliferator-activated Receptors . . . "The Journal of Biological Chemistry vol. 275, No. 46, Issue of Nov. 17, pp. 35715-35722, 2000.
Jeremy S. Duffield, et al., "Selective depletion of macrophages reveals distinct . . . "The Journal of Clinical Investigation vol. 115 No. 1 Jan. 2005.

\* cited by examiner

*Primary Examiner* — Elizabeth C Kemmerer
(74) *Attorney, Agent, or Firm* — Thomas Horstemeyer LLP; Lisa Pavento (57) ABSTRACT

The present disclosure elucidates that 34-mer PEDF suppresses hepatic stellate cells (HSCs) from activation by diminishing the levels of alpha-smooth muscle actin (α-SMC), collagen type 1, and monocyte chemoattractant protein-1 (MCP-1); and 44-mer PEDF promotes liver regeneration process by enhancing the replication of liver-derived progenitor cells (LDPCs). Accordingly, methods and compositions directing to the new use of the 34-mer PEDF or 44-mer PEDF in patients suffering from liver cirrhosis are provided herein.

7 Claims, 9 Drawing Sheets
(9 of 9 Drawing Sheet(s) Filed in Color)

USE OF PEDF-DERIVED POLYPEPTIDES FOR TREATING LIVER CIRRHOSIS

BACKGROUND OF THE INVENTION

1. Field of the Invention

The present disclosure relates to liver disease, and more particularly to the field of liver cirrhosis. The present disclosure relates to the use of molecules useful for the manufacture of a medicament for treating liver cirrhosis.

2. Description of Related Art

It is well known that liver is an organ having an extremely high ability of regenerating itself. However, in a case of chronic hepatic disease, liver undergo fibrosis during the regeneration process after continuous necrosis of hepatocytes, resulting in the suppression of normal hepatocyte regeneration. This may be due to an increase in extracellular matrix secreted by the activated hepatic stellate cells (HSCs) that involves in hepatic fibrosis. When HSCs are activated, they express α-smooth muscle actin and acquire smooth muscle property, whereby transforming themselves into myofibroblast-like cells.

Accordingly, if an agent or a molecule may inactivate HSCs, and/or revive liver regeneration process in patients having chronic cirrhosis condition, such agent or molecule represents a potential lead compound for the development of a medicament for treating liver cirrhosis.

SUMMARY

The present disclosure is based on the finding that PEDF-derived peptides may inactivate hepatic stellate cells (HSCs) or enhance replication or self-renewal activity of liver-derived progenitor cells (LDPCs) and thereby suppress hepatic fibrosis, promote liver regeneration and normalize the liver. The PEDF-derived peptides of this invention are, therefore, useful as an agent or a medicament for treating liver cirrhosis.

Accordingly, it is therefore an object of the present disclosure to provide a pharmaceutical composition for treating liver cirrhosis. The pharmaceutical composition includes an effective amount of a polypeptide having an amino acid sequence at least 90% identical to SEQ ID: 1 or SEQ ID NO: 2, or a plasmid nucleic acid encoding the polypeptide and a pharmaceutically acceptable carrier; wherein the polypeptide is capable of inactivating hepatic stellate cells (HSCs) or enhancing the replication of liver-derived progenitor cells (LDPCs).

According to one embodiment of the present disclosure, the plasmid nucleic acid is an adeno-associated viral vector. The polypeptide having an amino acid sequence at least 90% identical to SEQ ID: 1 is capable of inactivating HSCs by diminishing the levels of alpha-smooth muscle actin (a-SMC), collagen type I and monocyte chemoattractant protein-1 (MCP-1) as compared with that of the control; whereas the polypeptide having an amino acid sequence at least 90% identical to SEQ ID: 2 is capable of inducing self-renewal or replication of LDPCs. In one preferred embodiment, the polypeptide of SEQ ID NO: 1 is 34-mer PEDF, which corresponds to the segment of PEDF from amino acid residues 44 to 77; and the polypeptide of SEQ ID NO: 2 is 44-mer PEDF, which corresponds to the segment of PEDF from amino acid residues 78 to 121.

In another aspect, the present disclosure provides a method of treating liver cirrhosis in a subject. The method includes the step of administering to the subject in need thereof the pharmaceutical composition of this invention. In one preferred embodiment, the pharmaceutical composition of the present disclosure is administered parenterally every 1 to 10 days with a dose of 0.25 to 2.5 μg polypeptide/Kg of body weight or 10 μg to 1 mg plasmid nucleic acid/Kg body weight for at least 1 to 10 times. The subject is a mammal, preferably a human.

These and other features, aspects, and advantages of the present disclosure will become better understood with reference to the following description and appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features, aspects and advantages of the present invention will become better understood with reference to the following description, appended claims and the accompanying drawings, where:

FIG. 3 illustrates AAV-PEDF reduces $CCl_4$-induced inflammatory infiltration. Mice were injected with AAV-PEDF for 1 week and then treated with $CCl_4$ twice per week for 5 weeks. AAV-EGFP infected mice were used as control. Liver sections were immunostained by anti-CD68 antibody and counterstained with hematoxylin. Mice received $CCl_4$ or $CCl_4$ combining AAV-EGFP show a prominent macrophage infiltration. Mice received AAV-PEDF have mild macrophage infiltration. Original magnification: ×100.

FIG. 4 illustrates the suppression of primary rat HSC activation by PEDF in accordance with one embodiment of this invention. A: Immunoblot analysis of HSC lysates with antibodies as indicated. B: Left panels: Representative phase contrast micrographs show the modification of morphology of culture-activated HSCs by PEDF treatment for 48 h. Right panels: The filamentous actin of corresponding cells showed in left panels was stained by rhodamine-conjugated phalloidin. Original magnification ×200. C: Immunofluorescence analysis of the expression of α-SMA (green) in HSCs. DNA was visualized with Hoechst 33258 staining. Representative PEDF panels show that PEDF treatment causes reversal of the activated HSC morphology. D: Inhibitory effect of PEDF on HSC activation is reversed by PPAR γ siRNA. HSC-T6 cells were pretreated with siRNAs for 16 h before exposure to PEDF for an additional 48 h, and cells were then processed for RT-PCR analysis (blots 1 and 2) and immunoblot analyses (blots 3-7). "Mock" indicates transfection reagent-treated cells. E and F: AAV-PEDF prevents $CCl_4$- and TAA-induced HSC PPAR γ down regulation. Mice were injected with AAV-PEDF or AAV-EGFP for 1 week and then treated with $CCl_4$ or TAA twice per week for 3 weeks. (E) Representative pictures of four independent experiments show dual-immunofluorescent staining of HSCs by α-SMA (red), PPAR γ (green), and merged (yellow; PPAR γ-positive HSCs). Original magnification, ×400. (F) Percentage of PPAR γ-positive HSCs. *$P<0.002$ versus control mice; #$P<0.05$ versus AAV-EGFP.

FIG. 5 illustrates the suppression of the development of $CCl_4$-induced liver fibrosis by PEDF in accordance with one embodiment of this invention. A: Model of liver fibrosis. B: Representative Sirius red-stained liver sections. Comparing to AAV-EGFP infection, AAV-PEDF infection results in a significant reduction of fibrosis (original magnification, ×100). Representative pictures of at least 3 different experiments with six mice in each subgroup are shown. C: Estimation of liver fibrosis by the area of hepatic fibrosis detected by Sirius-red staining. D and E: AAV-PEDF prevents the accumulation of cirrhosis-related proteins in $CCl_4$-treated mice. Whole liver protein lysates were extracted for immunoblot analysis with indicated antibodies. Representative blots and densitometric analysis are from three independent experiments are shown. *$P<0.005$ versus control; #$P<0.002$ versus AAV-EGFP.

DESCRIPTION

These and other features, aspects and advantages of the present invention will become better understood with reference to the following description and the appended claims The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

DEFINITIONS

For convenience, certain terms employed in the specification, examples and appended claims are collected here. Unless defined otherwise, all technical and scientific terms used herein have the same meaning as commonly understood by one of the ordinary skill in the art to which this invention belongs.

The singular forms "a", "and", and "the" are used herein to include plural referents unless the context clearly dictates otherwise.

The term "treat" or "treating" as used herein includes preventative (e.g., prophylactic), curative or palliative treatment.

The term "encode" herein refers to a nucleic acid sequence which codes for a polypeptide sequence, or a portion thereof that contains amino acid sequence of at least 20 to 25 amino acids, more preferably at least 30 to 35 amino acids, and even more preferably at least 40 to 45 amino acids from a polypeptide encoded by the nucleic acid sequence. Also encompasses are polypeptide sequences which are immunological identifiable within a polypeptide encoded by the sequence.

The term "an effective amount" as used herein refers to an amount effective, at dosages, and for periods of time necessary, to achieve the desired therapeutically desired result with respect to the treatment of liver cirrhosis. It will be appreciated that the therapeutically effective amount of polypeptides of the present invention will vary from patient to patient not only for the particular polypeptide or composition selected, the route of administration, and the ability of the polypeptide (alone or in combination with one or more polypeptide or drugs) to elicit a desired response in the patient, but also factors such as disease state or severity of the condition to be alleviated, age, sex, weight of the patient, the state of being of the patient, and the severity of the pathological condition being treated, concurrent medication or special diets then being followed by the patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the compound or composition are outweighed by the therapeutically beneficial effects. Preferably, the polypeptides, nucleic acids encoding the same or compositions of the present invention are administered at a dosage and for a time such that the severity of the symptoms is decreased.

The term "replication" or "self-renewal" refers to a process by which liver-derived progenitor cells (LDPCs) duplicate their genetic material and then divide to yield two daughter cells. Animal cells usually do not replicate themselves unless certain growth factors are present. As exemplified in Examples 2.2 and 2.3 in the present disclosure, replication of LDPCs occurred only in the presence of PEDF or 44-mer PEDF, but not in the presence of 34-mer PEDF.

The terms "agent" or "medicament" are used interchangeably herein to refer to a polypeptide, a nucleic acid encoding the same or composition of which, when administered to a subject (human or animal) induces a desired pharmacological and/or physiological effect by local and/or systemic action.

The term "administered", "administering" or "administration" are used interchangeably herein to refer means either directly administering a polypeptide or a nucleic acid encoding the same, or a composition of the present invention, will form an equivalent amount of the polypeptide within the body.

The term "subject" refers to any animal (e.g., a mammal), including, but are not limited to humans, non-human primates, which is to be subjected under the treatment of this invention. Typically, "patient" and "subject" are used interchangeably herein in reference to a human subject.

In our previous study, we found that pigment-epithelium-derived factor (PEDF) exhibits a protective role in liver cirrhosis (Ho et al., Am J Pathol 2010 177(4): 1798-1811). The present finding confirms that such protective role of PEDF was mainly achieved by the N-terminal portion of PEDF, thus polypeptides were derived therefrom in the present disclosure with their functions respectively tested and confirmed. The thus derived PEDF polypeptides are suitable candidates for the development of a medicament or a therapeutically agent for treating liver cirrhosis.

Described herein are methods and compositions for treating liver cirrhosis of a subject by use of the PEDF-derived polypeptides or a plasmid nucleic acid encoding the polypeptides.

Thus in one aspect, the present invention is related to the use of a molecule, particularly a polypeptide or a nucleic acid, to manufacture a medicament or an agent for treating liver cirrhosis in a subject. In one embodiment, this invention is directed to the use of a polypeptide derived from PEDF for treating liver cirrhosis. The polypeptide has an amino acid sequence at least 90% identical to SEQ ID NO: 1 or SEQ ID NO: 2, and more preferably is at least 91%, 92%, 93%, 94%, 95%, 96%, 97%, 98%, 99% or 100% identical to the amino acid sequence set forth in SEQ ID NO: 1 or SEQ ID NO: 2. The polypeptide may be synthesized in accordance with any standard peptide synthesis protocol in the art. For example, the PEDF-derived polypeptides may be synthesized by use of a commercial solid-phase peptide synthesizer in accordance with the manufacturer's protocols. Alternatively, the polypeptide may be produced by recombinant technology. Any suitable plasmid vector may be used to practice this disclosure, and the selection of plasmids may be easily obtained by any skilled person in the related art without undue experimentation. Accordingly, in another embodiment of this invention, the use of a nucleic acid encoding the polypeptide of this invention is provided. The expressed polypeptide has an amino acid sequence at least 90% identical to SEQ ID NO: 1 or SEQ ID NO: 2, and more preferably is at least 91%, 92%, 93%, 94%, 95%, 96%, 97%, 98%, 99% or 100% identical to the amino acid set forth in SEQ ID NO: 1 or SEQ ID NO: 2. In one preferred example, the polypeptide having an amino acid sequence of SEQ ID NO: 1 is 34-mer PEDF. In another preferred example, the polypeptide having an amino acid sequence of SEQ ID NO: 2 is 44-mer PEDF.

Percentage of identity is a measure of the number of identical amino acids or nucleotides in an uninterrupted linear sequence of amino acids or nucleotides when compared to a target amino acid or nucleotide sequence of specified length. As used herein, "identity" of an amino acid sequence or a nucleotide sequence means that the compared amino acid/nucleotide residues in two separate sequences are identical. Thus, 100% identity means, for example, that upon comparing 50 sequential amino acids or nucleotides in two different molecules, both residues in all 50 pairs of compared amino acids or nucleotides are identical.

Any skilled person in this art may modify the synthesized or expressed recombinant polypeptides of this invention by methods (such as a computer simulation program) that predict the effect on polypeptide conformation of a change in polypeptide sequence, and thus may "design" or "modify" a PEDF-derived polypeptide based on the information disclosed herein by proposing and testing a modified PEDF-derived polypeptide to determine whether the modified PEDF-derived polypeptide retains a desired function or conformation. The PEDF-derived polypeptide may be modified specifically to alter a feature of the peptide unrelated to its physiological activity. For example, cystein residues can be substituted or deleted to prevent unwanted disulfide linkage. Similarly, certain amino acids can be changed and/or deleted without affecting the physiological activity of the peptide in this study (i.e., its ability to bind to a HSP specific autoantibody in an immunoassay). This invention thus encompasses functionally equivalent derivatives of PEDF-derived peptides synthesized in one embodiment of this invention, including peptides having conservative amino acid substitutions. Conservative substitutions of amino acids include substitutions made amongst amino acids within the following groups: (a) M, I, L, V; (b) F, Y, W; (c) K, R, H; (d): A, G; (e) S, T; (f) Q, N; (g) E, D; and (h) C, M.

Accordingly, pharmaceutical compositions comprising the PEDF-derived polypeptides of the present disclosure are provided. In one embodiment, the composition comprises a polypeptide having an amino acid sequence at least 90% identical to SEQ ID NO: 1 or a nucleic acid encoding the polypeptide, in which the polypeptide is capable of inactivating HSCs by diminishing the expressed levels of alpha-smooth muscle actin (α-SMC), collage type I (e.g., alpha1(I) collagen (Col1a1)), and monocyte chemoattractant protein-1 (MCP-1) as compared with that of the control, that is, the respective levels of α-SMC, collage type I, and MCP-1 of a healthy subject. In one preferred embodiment, the polypeptide of SEQ ID NO: 1 is 34-mer PEDF, which corresponds to the segment of PEDF from amino acid residues 44 to 77.

In another embodiment, the composition comprises a polypeptide having an amino acid sequence at least 90% identical to SEQ ID NO: 2 or a nucleic acid encoding the polypeptide, in which the polypeptide is capable of inducing replication of LDPCs. The replication of LDPCs is manifested in having a detected level of autofluorescence or forming a LDPC colony after a prolonged period of culture, such as at least 30, 35 or 40 days in culture, while retaining their ability of differentiating into hepatocytes. In one preferred embodiment, the polypeptide of SEQ ID NO: 2 is 44-mer PEDF, which corresponds to the segment of PEDF from amino acid residues 78 to 121.

The pharmaceutical composition is prepared in accordance with acceptable pharmaceutical procedures, such as described in Remington's Pharmaceutical Sciences, 17$^{th}$ edition, ed. Alfonoso R. Gennaro, Mack Publishing Company, Easton, Pa. (1985). Pharmaceutically acceptable excipients are those that are compatible with other ingredients in the formulation and biologically acceptable.

The polypeptides (e.g., the polypeptide having an amino acid sequence of SEQ ID NO: 1 or SEQ ID NO: 2 as described above) or the nucleic acid encoding the polypeptides of this invention may be administered orally, parenterally, transdermally, rectally or by inhalation, alone or in combination with conventional pharmaceutically acceptable excipients. In preferred embodiments, the polypeptides or nucleic acids encoding the same of this invention are administered parenterally to the subject.

The polypeptides or nucleic acids encoding the same of the present invention may also be formulated into liquid pharmaceutical compositions, which are sterile solutions or suspensions that can be administered by, for example, intravenous, intramuscular, subcutaneous, interperitoneal or intra-cerebella injection. Oral administration may be either liquid or solid composition form.

The pharmaceutical compositions of this invention may be formulated into a variety of dosage forms for topical application. A wide variety of dermatologically acceptable inert excipients well known to the art may be employed. The topical compositions may include liquids, creams, lotions, ointments, gels, sprays, aerosols, skin patches, and the like. Typical inert excipients may be, for example, water, ethyl alcohol, polyvinyl pyrrolidone, propylene glycol, mineral oil, stearyl alcohol and gel-producing substances. All of the above dosages forms and excipients are well known to the pharmaceutical art. The choice of the dosage form is not critical to the efficacy of the composition described herein.

The pharmaceutical compositions of this invention may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinylpyrrolidone; dextran; guar gum; pectins; starches; and cellulosic polymers.

The pharmaceutical compositions of this invention may also be formulated into an inhaler aerosol formulation for drug delivery through nasal mucosal membranes. Suitable propellants and/or co-solvents for solubilizing the active agents such as the polypeptides or nucleic acid encoding the same of this invention in medicinal aerosol formulations are well known in this art. Typical propellants are hydrofluoroalkanes such as 1,1,1,2-tetrafluoroethane (HFA-134a), 1,1,1,2,3,3,3-heptafluoropropane (HFA-227ea). pentafluoroethane (HFA-125), 1,1-difluoroethane (HFA-152a), difluoromethane (HFA-32) and the like. Typical co-solvents include, but not limited to, alcohols, polyols, alkoxy derivatives, fatty acid alkyl esters, polyalkylene glycols, dimethylsulphoxide and the like.

Accordingly, this invention also provides methods of treating mammals, preferably humans, for liver cirrhosis, which comprises the step of administrating the pharmaceutical composition of this invention that contains a polypeptide described above or a nucleic acid encoding the same to the mammals in need thereof. Accordingly, such composition is administered to a mammal, preferably human, by any route that may effectively transports the active ingredient(s) of the composition to the appropriate or desired site of action, such as oral, nasal, pulmonary, transdermal, such as passive or iontophoretic delivery, or parenteral, e.g., rectal, depot, subcutaneous, intravenous, intramuscular, intranasal, intra-cerebella, ophthalmic solution or an ointment. Further, the administration of the polypeptides or nucleic acids encoding the same with other active ingredients may be concurrent or simultaneous. In one example, the pharmaceutical composition of the present disclosure is administered parenterally every 1 to 10 days with a dose of 0.25 to 2.5 µg polypeptide/Kg of body weight or 10 µg to 1 mg plasmid nucleic acid/Kg body weight for at least 1 to 10 times.

The present invention will now be described more specifically with reference to the following embodiments, which are provided for the purpose of demonstration rather than limitation.

EXAMPLES

Materials and Methods

Animal Model of Liver Cirrhosis

For the induction of liver fibrosis, 6-weeks old BALB/c mice (6 mice per experimental condition) were injected intraperitoneally twice a week with either $CCl_4$ solution (5 ml/kg body weight as a 1:4 mixture with olive oil) or thioacetamide (TAA, 200 mg/kg) for 3 weeks. The experimental procedures were approved by the Mackay Memorial Hospital Review Board (Tamsui Town, Taiwan, R.O.C.) and conducted according to national animal welfare regulations.

Construction of Adeno-Associated Virus PEDF (AAV-PEDF)

AAV-PEDF was constructed and purified according to similar methods described before (Xiao X et al., J Virol 1998, 72:2224-2232). Briefly, human PEDF and enhanced green fluorescent protein (EGFP) cDNAs were obtained from plasmid pET-15b-PEDF and p-EGFP-N1 (Clontech, Mountain View, Calif., USA), respectively (Tsao et al., Life Sci 2006, 79:545-550). The PEDF cDNA was subcloned into the BamHI/NotI site of the AAV packaging plasmid (pAAV-D+), allowing transcription of PEDF to be driven by the cytomegalovirus promoter. To construct recombinant AAV, pAAV-D (+)-hPEDF and AAV helper plasmids (pXR5 and pXX6) were co-transfected into human embryonic kidney 293T cells. This cloning procedure was also used to generate AAV-EGFP. The expression of AAV-PEDF in 293T cells was confirmed by polymerase chain reaction (PCR) and immunoblotting. The AAV particles were produced by multiple freeze/thaw cycles and cesium chloride density gradient purification, and titers were determined by dot-blot assay in the range of $1.0$ to $3.0 \times 10^{13}$ viral particles/ml. The expression of AAV was examined by immunoblotting of liver proteins from mice injected with AAV-PEDF ($2 \times 10^{12}$ viral particles) through the tail vein. Prominent human PEDF expression was found 2 weeks after AAV infection.

Human 34-mer PEDF and 44-mer PEDF

Synthetic human 34-mer PEDF and 44-mer PEDF (purity >95%) were purchased from GenScript (Piscataway, N.J., USA). The N-terminus and the C-terminus of each peptides were respectively acetylated and amidated, so as to stabilize the peptides, and were stored in DMSO as 5 mM stock solution at −20° C. until use.

Isolation and Culture of Primary Hepatic Stellate Cells (HSCs)

Primary HSCs were isolated by in situ perfusion with collagenase and pronase from livers of male Sprague-Dawley rats (300-450 g), followed by a 25%/50% Percoll gradient centrifugation at 4° C. HSCs were isolated from the upper layer of the discontinuous Percoll density gradient as previously described method (Titos et al., FASEB J 2003 17:1745-1747). Then cells were re-suspended in Dulbecco's modified Eagle's medium (DMEM) supplemented with 10% fetal bovine serum (FBS) and 1% penicillin/streptomycin and plated on 100-mm plastic dishes. Cell purity was verified to be approximately 95-98% by vitamin A fluorescence on day 2 after isolation. HSCs were activated by culturing the cells on plastic for 10 days and then passaged by trypsin-EDTA treatment. Subsequently, the activated HSCs were incubated in 10% FBS-DMEM for 2 days and then used for further experiments.

HSC-T6 cells, a rat immortalized HSC, retained all features of activated HSCs and was kindly provided by Dr. Friedman S L (Kim et al., J Biol Chem 1998 273:33750-33758). HSC-T6 cells were grown in Waymouth medium supplemented with 10% FBS at 37° C. in a humidified atmosphere of 5% $CO_2$.

Isolation and Culture of Liver-derived Progenitor Cells (LD-PLs)

Liver cells from Sprague Dawley rats were harvested by 2-step in situ collagenase perfusion technique. The cells were then washed in phosphate buffered saline and centrifuged (50 g for 5 minutes) twice at room temperature. The cells were not further subjected to any fractionation as previously described (Sahin M B et al., Liver Transpl. 2008 14(3):333-45). Freshly isolated rat liver cells were cultured in a medium consisting of 75% Dulbecco's modified Eagle's medium (DMEM) and 25% MCDB 201 (Sigma-Aldrich) supplemented with 10% fetal bovine serum, 1 mg/mL of bovine serum albumin (BSA; Sigma), 100 μM of β-mercaptoethanol (Gibco, Carlsbad, Calif.), 25 mM of 4-2-hydroxyethyl-1-piperazineethanesulfonic acid (HEPES), 5 mM of Nicotinamide (Sigma-Aldrich), 1% SITE liquid medium (Sigma-Aldrich), and penicillin (100 μg/ml)/streptomycin (100 μg/ml; Invitrogen, Carlsbad, Calif.) on Type I collagen (Sigma, St. Louis, Mo.) coated tissue culture plates or dishes at a density of $1 \times 10^4$ cells/$cm^2$ at 37° C. in 5% $CO_2$.

Immunohistochemistry

Formalin-fixed, paraffin-embedded mice liver specimens were deparaffinized in xylene and rehydrated in a graded series of ethanol. Slides were blocked with 10% goat serum for 60 min and then incubated with primary antibody against CD68 (ab53444; Abcam, Cambridge, Mass.) overnight at 4° C. The slides were then incubated with the appropriate peroxidase-labeled goat immunoglobulin for 20 min and then incubated with chromogen substrate (3,3'-diaminobenzidine) for 2 min before counterstaining with hematoxylin. Quantification was estimated based on high quality images (1208×960 pixels buffer) captured using a Nikon Eclipse 80i light microscope.

Sirius-Red Staining

Deparaffinized liver tissue sections were stained for 1 h in 0.1% (w/v) Sirius red (Sigma, St. Louis, Mo.) in a saturated aqueous solution of picric acid and then rinsed for 30 min in 0.01 N acetic acid to remove unbound dye. For semi-quantitative analysis of liver fibrosis, 10 fields from each slide were randomly selected under a light microscope, and the red-stained area per total area ($mm^2/mm^2$) was measured using the Image-Pro Plus 4.5.1 system.

Immunofluorescence

Deparaffinized liver tissue sections or 4% paraformaldehyde fixed HSCs were blocked with 10% goat serum and 5% BSA for 1 h. Dual staining was done using primary antibodies against human PEDF (se-59641; Santa Cruz Biotechnology, CA, USA) or α-SMA (ab5694 or ab7817; Abcam), PPARγ (sc-7273; Santa Cruz Biotechnology), albumin (sc-46295; Santa Cruz Biotechnology) or cytokeratin (CK) 18 (GTX112978; GeneTex, Inc.) at 37° C. for 2 h, followed by incubation with the appropriate rhodamine- or FITC-conjugated donkey IgG for 1 hr at room temperature. Nuclei were located by counterstaining with Hoechst 33258 for 7 min. Images were captured using a Zeiss epifluorescence microscope with a CCD camera.

Semi-Quantitative Reverse Transcriptase (RT)-PCR

The total RNA was extracted from cells using the TRIzol (Invitrogen, Carlsbad, Calif.). Synthesis of cDNA was performed with 1 μg of total RNA at 50° C. for 50 min using oligo (dT) primers and reverse transcriptase (Superscript III; Invitrogen) following the manufacturer's instructions. cDNA was equalized in an 18-26 cycle amplification reaction (denaturation, 20s, 94° C.; annealing, 30s, 57° C.; and polymerization, 40s, 72° C.) with mouse PEDF primers 5'-cctctgttactgccct-gag-3' (forward, SEQ ID NO: 3)/5'-gcctgcacccagttgttaat-3' (reverse, SEQ ID NO: 4) and rat PPARγ primers 5'-ccctg-gcaaagcatttgtat-3' (forward, SEQ ID NO: 5)/5'-actggcaccct-tgaaaaatg-3' (reverse, SEQ ID NO: 6) yielding 221-bp product. The number of cycles for the primer set was chosen to be in the linear range of amplification. The PCR products were electrophoresed in a 2% agarose gel containing ethidium bromide and visualized by UV illumination. The intensities of the PCR products were quantified using a FUJI LAS-3000 densitometer and Multi Gauge Ver. 1.01 software (Fujifilm, Tokyo, Japan).

Immunoblot Analysis

Cells were scraped into lysis buffer (150 μL/35-mm well) containing 20 mM HEPES (pH 7.4), 1% SDS, 150 mM NaCl, 1 mM EGTA, 5 mM β-glycerophosphate, 10 mM sodium pyrophosphate, 10 mM sodium fluoride, 100 mM sodium orthovanadate, 10 μg/mL leupeptin, and 10 μg/mL aprotinin. The lysate was incubated on ice for 15 min. Total cell lysate was also separated into cytoplasmic and nuclear fractions using the NE-PER nuclear and cytoplasmic extraction kit (Pierce, Rockford, Ill.) according to the manufacturer's instructions. Each cellular fraction was then resolved by SDS-PAGE and then electrotransferred to polyvinylidene difluoride membranes (Millipore, Bedford, Mass.) and processed for immunoblot analysis. Antibodies used in the immunoblot study included human PEDF (sc-59641; Santa Cruz Biotechnology), mouse PEDF (sc-74253; Santa Cruz Biotechnology), type I collagen 1A1 (sc-25974; Santa Cruz Biotechnology), α-SMA (ab5694 or ab7817; Abcam), PPARγ••(sc-7273; Santa Cruz Biotechnology), MCP-1 (ab7202; Abcam Ltd), α-actin (Sigma), epithelial cell adhesion molecule (EpCAM; sc-66020; Santa Cruz Biotechnology), hepatocytes nuclear factor and (HVF)3-β (sc-6554; Santa Cruz Biotechnology). Proteins of interest were detected using the appropriate IgG-HRP secondary antibody and ECL reagent. X-ray films were scanned on a Model GS-700 Imaging Densitometer (Bio-Rad Laboratories, Hercules, Calif.) and analyzed using Labworks 4.0 software. For quantification, blots from at least three independent experiments were used.

Actin Staining

After treatment, primary rat HSCs were fixed for 2 h with 4% paraformaldehyde, washed by PBS and then permeabilized for 5 min with 0.1% Triton X-100. Changes in F-actin structures were detected by 0.33 mM rhodamine-conjugated phalloidin (Sigma) for 1 h at room temperature. Stained F-actin was visualized using a Zeiss Axiovert 25 microscope.

PPARγ•Small Interfering RNA Treatment

Sub-confluent HSC-T6 cells were transfected with a rat PPAR••siRNA (sense sequence, SEQ ID NO: 7: 5'-CAC-CAUUUGUCAUCUACGATT-3'/antisense sequence, SEQ ID NO: 8: 5'-UCGUAGAUGACAAAUGGUGTT-3') or a mixture of four rat PPARγ siRNAs (SMART-pools; Dharmacon Research, Inc., Lafayette) using INTERFERin siRNA transfection reagent (PolyPlus-Transfection, San Marcos, Calif.) according to the manufacture's instructions. The final concentration of siRNA was 10 nM. A species-specific siCONTROL nontargeting siRNA (Dharmacon) was utilized as a negative control. At 16 hr after siRNA transfection, cells were resuspended in fresh media for a recovery period of 24 hrs.

Statistics

Results are mean±standard error of the mean (SEM). ANOVA and linear regression were used for statistical comparisons. P <0.05 was considered significant.

Example 1

Figure 1:
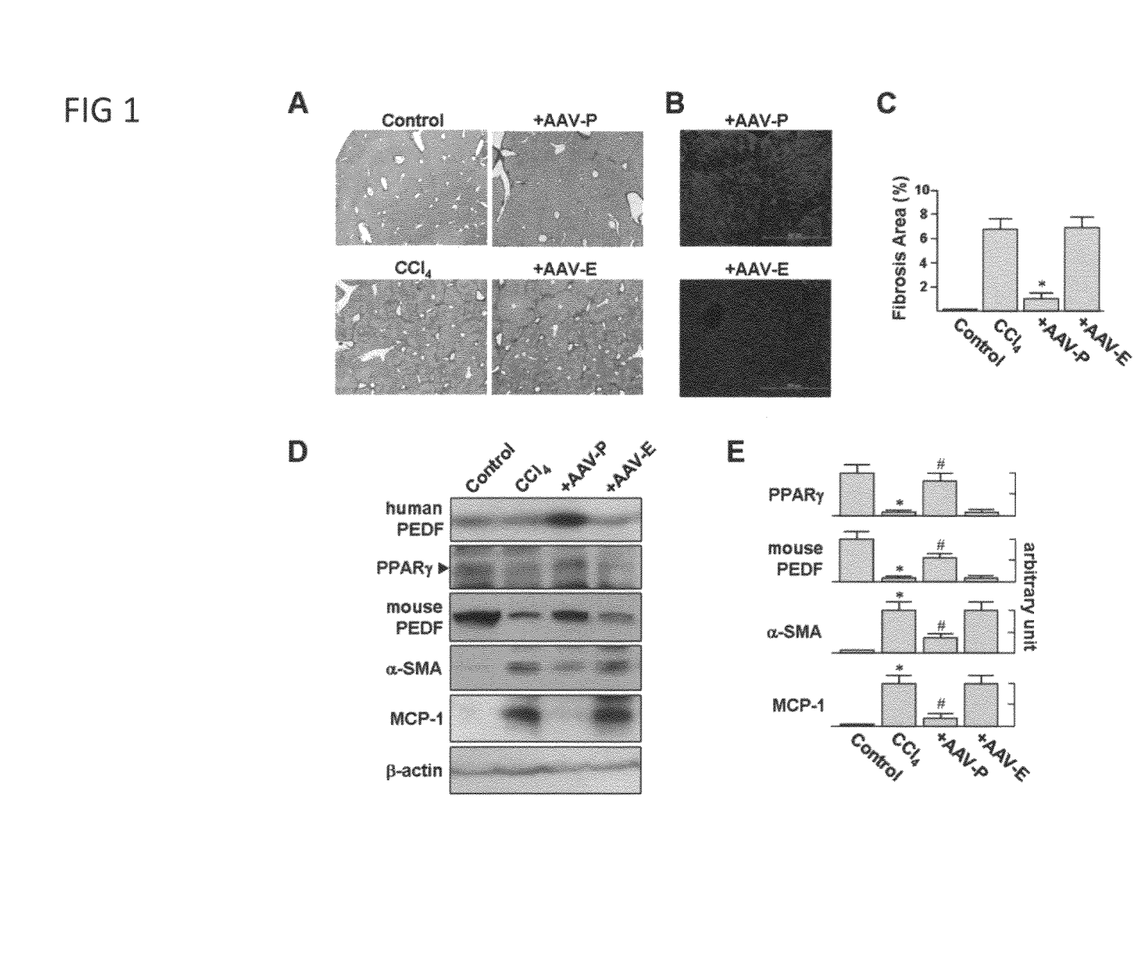
FIG. 1 illustrates the protection of Adeno-associated virus (AAV)-PEDF pretreatment on mice from $CCl_4$-induced hepatic fibrosis in accordance with one embodiment of this invention. A: Collagen deposition in mice's liver stained by Sirius-red and hematoxylin (original magnification, ×40). B: Immunofluorescence analysis of liver tissue revealed the expression of human PEDF in AAV-PEDF-injected animals (original magnification, ×200). C: The average percentages of area stained positive with Sirius-red in AAV-PEDF-injected animals and that of the control group. *$P < 0.05$ versus AAV-EGFP. D and E: Immunoblot analysis of liver lysates with antibodies as indicated. Representative blots and densitometric analysis from four independent experiments are shown. *$P<0.001$ versus control; #$P<0.001$ versus AAV-EGFP.

PEDF is an Intrinsic Antifibrosis Factor Targeting Hepatic Stellate Cells 1.1 PEDF Prevents $CCl_4$— and Thioacetamide-induced Hepatic Fibrosis To supplement liver with PEDF, human PEDF gene was delivered into liver cells by the constructed AAV-PEDF vector described above in Materials and Methods. The same vector was used to deliver the EGFP gene in control experiments. After intraperitoneal injection of mice with $CCl_4$ twice per week for 3 weeks, Sirius red and hematoxylin-stained liver slices revealed a marked parenchymal injury and bridging fibrosis (FIG. 1A). When mice were injected with AAV-PEDF for 1 week before $CCl_4$ treatment for additional 3 weeks, immunofluorescence staining using an anti-human PEDF antibody revealed that local synthesis of PEDF (green) in hepatocytes was achieved by PEDF gene delivery (FIG. 1B). At the same time, reduced parenchymal injury and smaller areas of fibrosis were observed as compared with animals receiving $CCl_4$ plus AAV-EGFP injection (FIG. 1C; 1.1±0.5% versus 6.9±0.9%).

To determine whether reduced fibrosis in mice infected with AAV-PEDF represents suppressed HSC activation, the levels of α-SMA and MCP-1 in liver protein extracts were evaluated (FIGS. 1D and 1E). It was found that AAV-PEDF injection diminished α-SMA and MCP-1 levels by a factor of 3.1 and 5, respectively, as compared to that in $CCl_4$+EGFP group. Moreover, AAV-PEDF pretreatment also significantly prevented the decline of peroxisome proliferator-activated receptor gamma (PPARγ)•levels (FIGS. 1D and 1E). PPARγ•is a transcription factor that expresses in quiescent HSCs, and its expression and activity dramatically decreases in myofibroblast-like, activated HSCs (Miyahara et al., J Biol Chem 2000 275:35715-35722).

Figure 2:
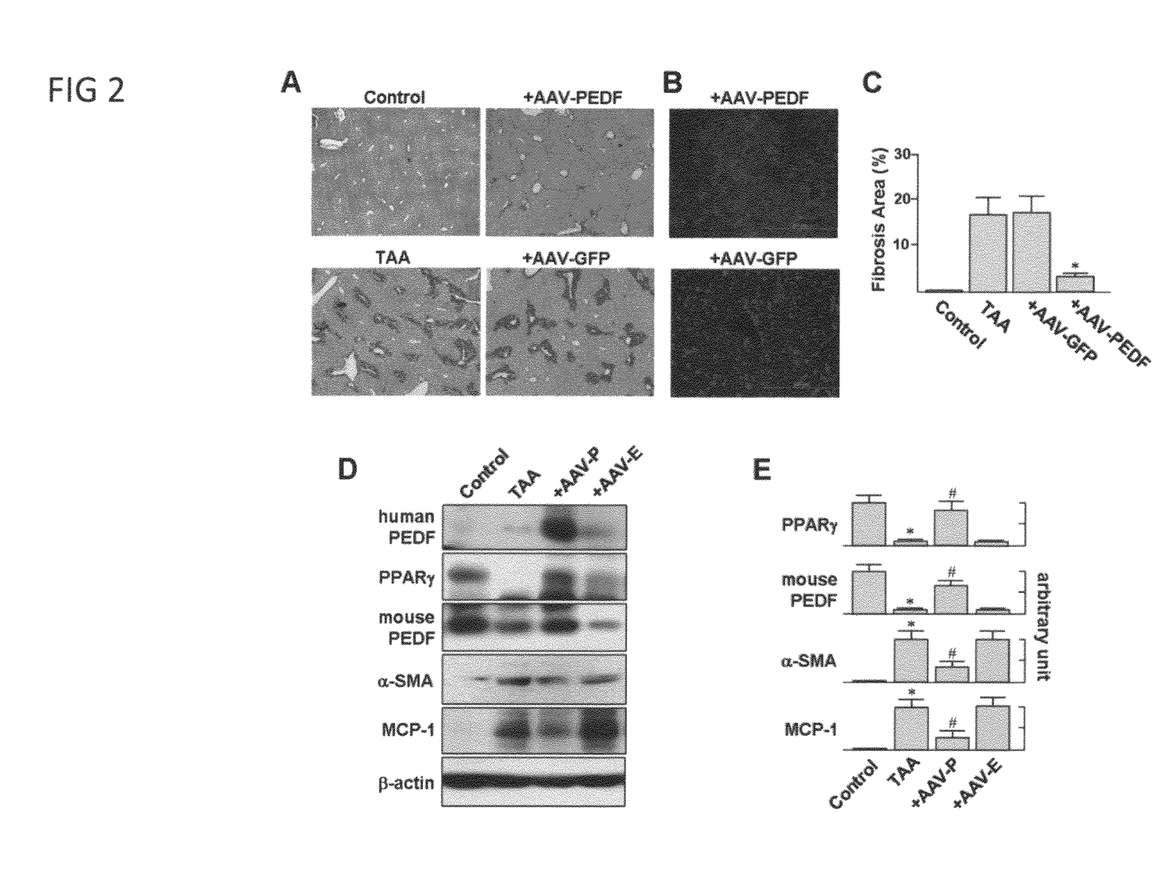
FIG. 2 illustrates the AAV-PEDF prevents liver fibrosis and suppresses the accumulation of cirrhosis-related proteins in thioacetamide (TAA)-treated mice. A: AAV-PEDF prevents liver fibrosis. Morphometric analysis of hepatic fibrosis was assessed by detection of collagen content in liver using Sirius-red staining (original magnification, ×40). B: The distribution of AAV-PEDF expressed human PEDF in adjacent liver sections was detected by immunoflorescence staining using a human PEDF-specific antibody (original magnification, ×200). C: Estimation of collagen deposition area. *$P<0.05$ compared with AAV-EGFP. D and E: Liver extracts were subjected to immunoblot analysis with antibodies as indicated. Representative blots and densitometric analysis from three independent experiments are shown. *$P<0.05$ versus control; #$P<0.001$ versus AAV-EGFP.

The protective effect of AAV-PEDF was also reproducible in TAA-induced liver fibrosis, indicated by reduced Sirius-red staining and partial repression of TAA-induced α-SMA and MCP-1 expression in liver sections (FIG. 2).

Figure 3:
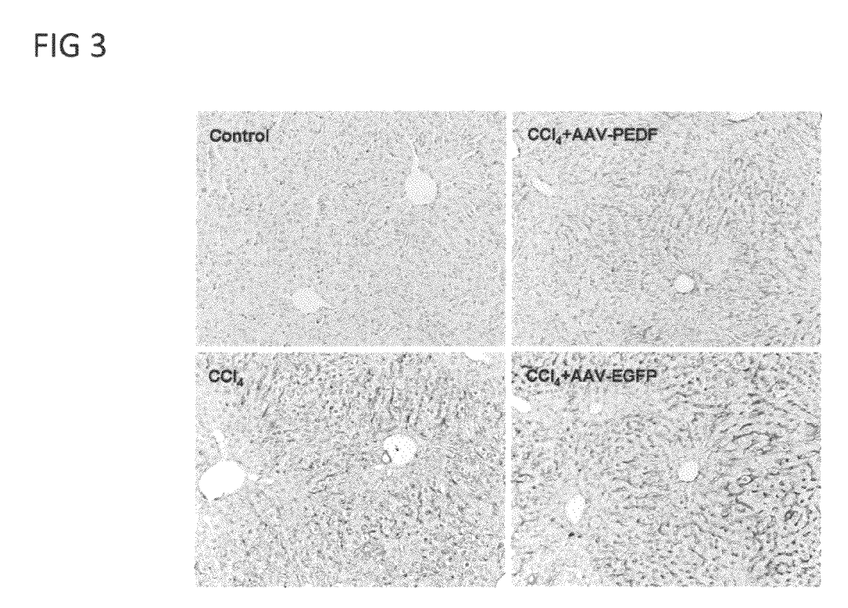

It has been established that mice treated with $CCl_4$ over 4 week exhibited a higher degree of inflammation with a macrophage infiltration (Duffield et al., J Clin Invest 2005 115: 56-65). Immunohistochemistry analysis of liver sections from mice received $CCl_4$ treatment for 5 weeks using anti-CD68 antibody exhibited an obvious macrophage infiltration in injured area (FIG. 3). However, liver sections of mice received AAV-PEDF displayed a reduction in macrophage infiltration in the injured area as compared with that in $CCl_4$ or $CCl_4$+AAV-EGFP groups. This observation is consistent with the inhibitory effect of AAV-PEDF on $CCl_4$-induced parenchymal injury and MCP-1 protein expression (FIGS. 1A and 1D). Taken together, these data suggest that AAV-PEDF may ameliorate inflammation and fibrosis.

1.2 PEDF Suppresses the Activation of Hepatic Stellate Cells (HSCs)

The protective effect of PEDF against liver fibrosis described above in Example 1.1 suggests that PEDF prevents the activation of HSCs through induction of PPARγ. This is indeed observed in culture-activated primary rat HSCs that PEDF treatment for 48 hours significantly reduced α-SMA, Col1a1, and MCP-1 expression as compared with solvent treatment alone (FIG. 4A).

Figure 4:
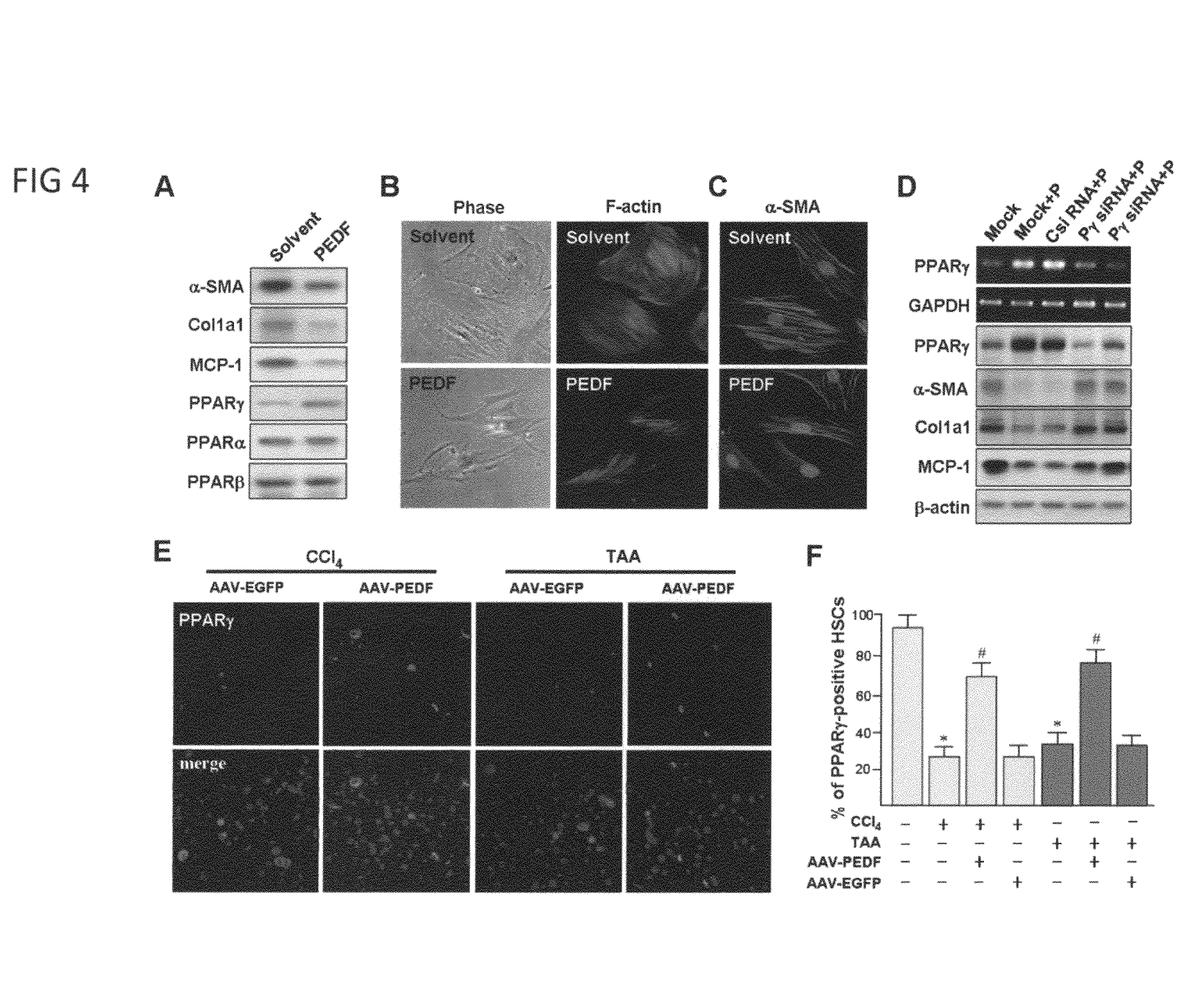

When cell morphology was compared, culture-activated HSCs assumed an enlarged, flattened morphology, whereas PEDF exposure resulted in a dendritic-like morphology with retracted cytoplasm (FIG. 4B). We further examined the stress fiber architecture, a characteristic feature of HSC activation, by rhodamine-phalloidin staining of filamentous (F-) actin and immunofluorescent staining of α-SMA (FIGS. 4B and 4C). Culture-activated HSCs displayed prominent stress fibers and α-SMA staining, whereas PEDF exposure reduced stress fiber and α-SMA formation, indicating suppression of the activation of HSCs. Also, PEDF treatment for 48 hours induced mRNA and protein expression of PPARγ•in an immortalized rat HSC cell, HSC-T6 cells (FIG. 4D). HSC-T6 cells pretreated with PPARγ•siRNA for 16 hours before exposure to PEDF significantly reduced the suppressive effects of PEDF on HSC activation as assayed by a-SMA, Col1a1 and MCP-1 (FIG. 4D). In animals with chemical-induced liver fibrosis, immunohistochemical staining results indicated that control animals received AAV-EGFP had fewer PPARγ-positive HSCs, much less than animals received AAV-PEDF after $CCl_4$ exposure (FIGS. 4E and 4F; 27±5% versus 70±8%) or TAA treatment (34±4% versus 77±5%).

Figure 5:
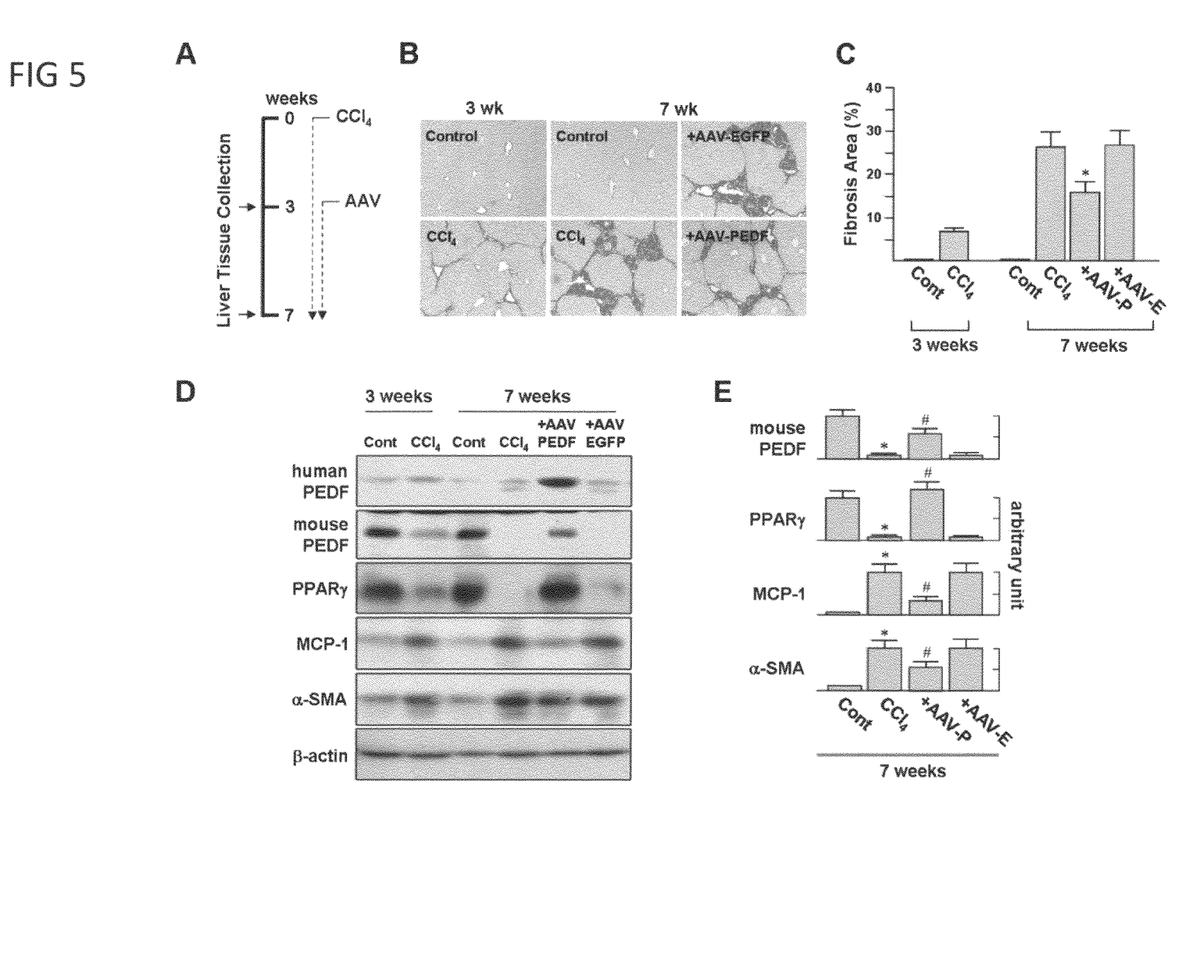

1.3 AAV-PEDF Suppresses the Development of Fibrosis in $CCl_4$-Treated Mouse Liver In a protocol designed to mimic the therapy of cirrhosis, mice were injected with $CCl_4$ twice a week for 3 weeks to establish hepatic fibrosis. Then, mice received AAV via tail vein and were continuously injected with $CCl_4$ for further 4 weeks (FIG. 5A). Fibrotic area quantified by Sirius-Red staining was found to be significantly increased by 3.3-fold in mice administrated with $CCl_4$ for 7 weeks comparing to mice treated for only 3 weeks (FIGS. 5B and 5C). Importantly, mice received AAV-PEDF caused a significantly decrease of fibrotic area compared to AAV-EGFP group at week 7 (FIG. 5C; 16.5±1.6% versus 27.0±3.1%).

Human PEDF protein in the mouse liver infected with AAV-PEDF was demonstrated by immunoblotting (FIG. 5D). The immunoblots also showed significantly higher expressed PPARγ•and mouse PEDF in AAV-PEDF-infected mice compared with AAV-EGFP groups, whereas considerably decreased α-SMA and MCP-1 protein expression in AAV-PEDF groups by a factor of 1.8-fold and 3.4-fold, respectively, as compared with AAV-EGFP groups at the week 7 (FIG. 5E). The reduced α-SMA protein levels seen in AAV-PEDF-infected mice correlate a milder collagen deposition, suggesting that fibrosis progression is suppressed by AAV-PEDF infection.

Example 2

34-mer and 44-mer PEDF Function Similarly to PEDF by Respectively Inactivating Hepatic Stellate Cells (HSCs) and Enhancing Self-renewal Activity of Liver-derived Progenitor Cells (LDPCs)

2.1 Human 34-mer PEDF Suppresses Activation of Hepatic Stellate Cells

Figure 6:
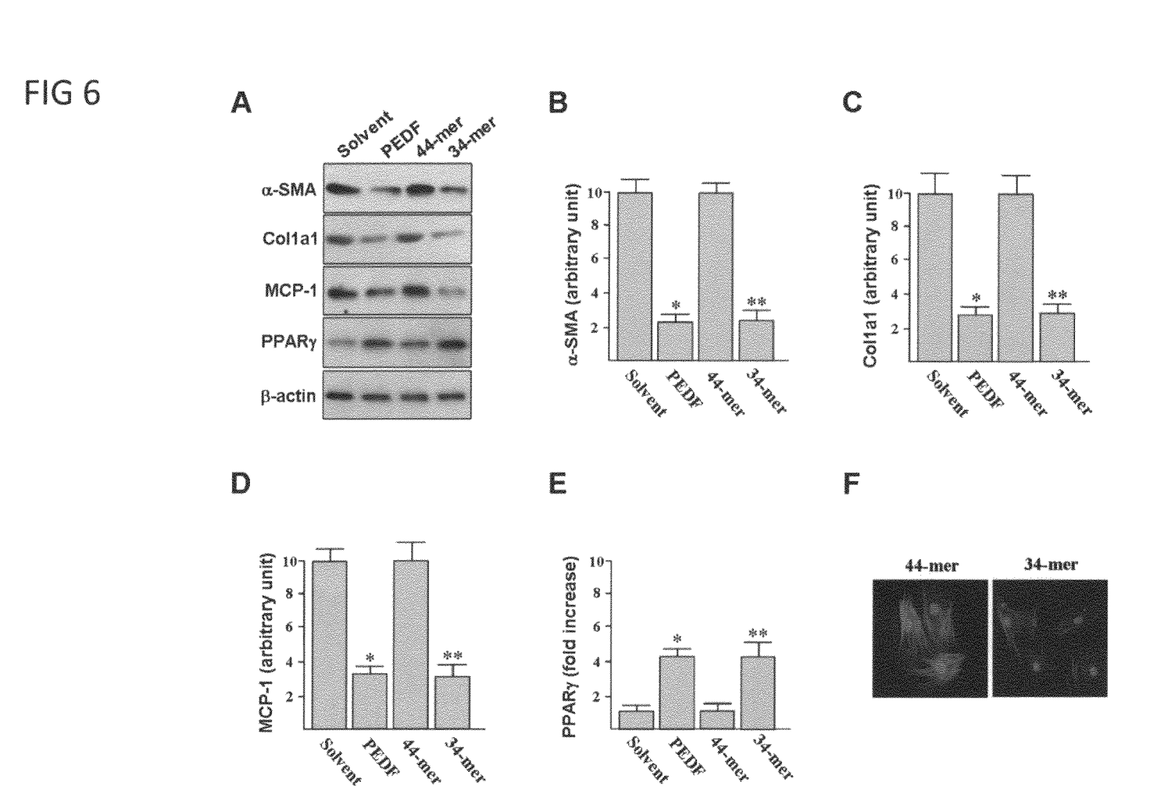
FIG. 6 illustrates the inactivation of primary rat hepatic stellate cells (HSCs) by 34-mer PEDF in accordance with one embodiment of this invention. A-E: Immunoblot analysis with antibodies as indicated. Representative blots and densitometric analysis from 3 independent experiments are shown. *$P<0.05$ vs. solvent-treated HSCs. **$P<0.05$ vs. 44-mer-treated HSCs. F: Immunofluorescence analysis of the expression of -SMA (green) in HSCs. DNA was visualized with Hoechst 33258 staining. Representative 34-mer panel depicts that 34-mer treatment causes reversal of the activated HSC morphology.

To verify whether the PEDF-derived peptides, particularly, 34-mer PEDF and 44-mer PEDF, may prevent HSCs from activation, culture-activated primary rat HSCs were treated with 4.5 nM PEDF, 50 nM 44-mer, 50 nM 34-mer or PEDF solvent (20 mM Tris/HCl, pH 7.4, 100 mM NaCl) for 48 hours. Immunoblot analysis revealed that 34-mer PEDF similar to PEDF reduced the expressions of α-SMA, Col1a1, and MCP-1; and enhanced the amounts of PPARγ as compared with solvent treatment alone (FIG. 6A-E). 44-mer PEDF does not possess such effects. Immunofluorescent assay also confirmed that 34-mer PEDF reduced the levels of α-SMA in culture-activated HSCs as compared with 44-mer PEDF treatment (FIG. 6F). Such result is consistent with the finding in Example 1 that PEDF prevents HSCs from activation by induction of PPARγ.

Figure 7:
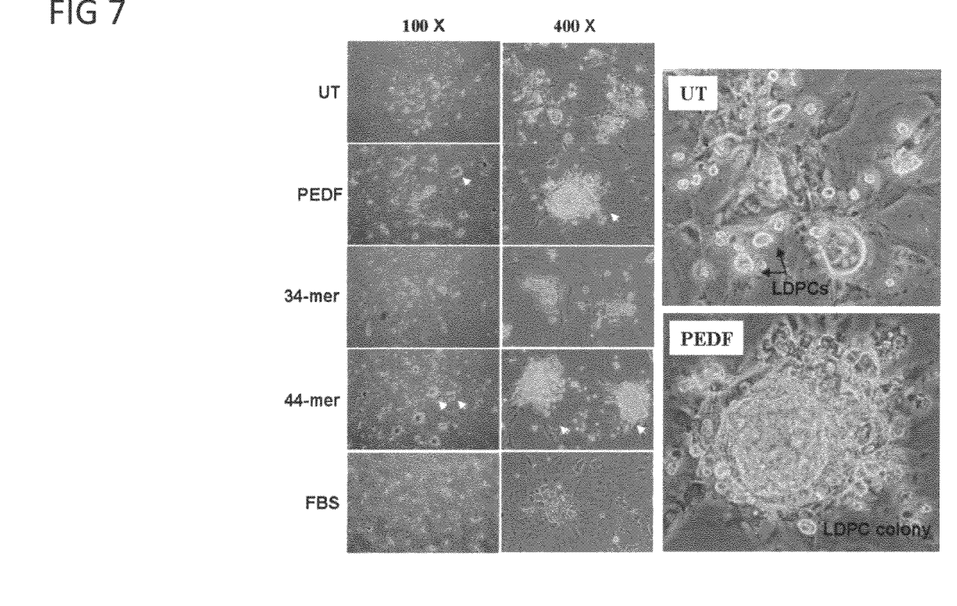
FIG. 7 illustrates the comparison of clonogenic capacity of liver cell under various culture conditions in accordance with one embodiment of this invention. Representative images taken under phase-contrast microscope are from three independent experiments. Original magnification, 100X and 400X as indications. LDPCs: liver-derived progenitor cells.

2.2 Human 44-mer PEDF Enhances Formation of Liver-Derived Progenitor Cells (LDPCs) Colony To verify the function of 44-mer PEDF, primary rat liver cells were isolated in accordance with steps described above and cultivated (about $1\times10^5$ per well of 6-well plate; $1\times10^4$ cells/cm$^2$) in a conventional basal medium, which was further supplemented with 4.5 nM PEDF, 50 nM 34-mer PEDF, 50 nM 44-mer PEDF or 10% FBS. Medium was changed every 3 days. After being placed in culture for 11 days, clonogenic capacity of liver cells was continuously monitored by phase-contrast microscopy. During this time period, liver-derived progenitor cells (LDPCs) began markedly emerged in primary liver cultures while hepatocytes started dying out. Few colonies were formed by liver cells when continuously cultivated in basal medium, or medium supplemented with 34-mer or FBS. On the other hand, liver cells stimulated with PEDF or 44-mer exhibited dense colonies of LDPCs (consisting of about 25-150 cells) in culture dish (FIG. 7).

2.3 Human 44-mer PEDF and PEDF Enhance Self-Renewal Activity of LDPCs

It has been reported that LDPCs may not be expanded in conventional basal medium, unless growth factor(s) were added therein (Sahin et al., Liver Transpl. 2008 14(3):333-45). To test the self-renewal property of PEDF derived peptides on LDPCs, liver cells were isolated and grown in separate medium including 4.5 nM (200 ng/ml) PEDF, 50 nM 34-mer or 50 nM 44-mer for two passages, which took a period of 35 days. The newly produced LDPCs in the cultured cells were confirmed by the detection of autofluorescence emitted therefrom; as well as two LDPC markers, which are epithelial cell adhesion molecule (EpCAM) and hepatocytes nuclear factor 3•••(HNF3)-β, by immunoblot analysis. Results are provided in FIG. 8.

Figure 8:
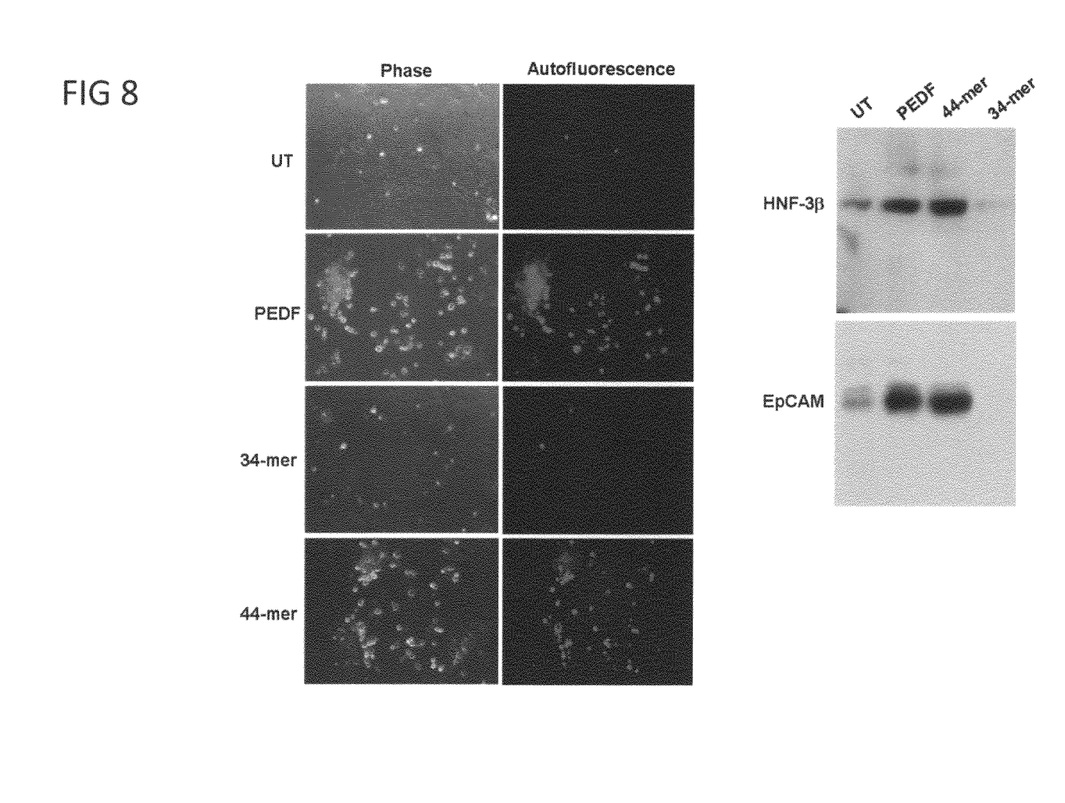
FIG. 8 illustrates the self-renewal property of PEDF and 44-mer PEDF on LDPCs in accordance with one embodiment of this invention. Left Panels. Representative PEDF and 44-mer PEDF panels exhibited high autofluorescence cells (a LDPC marker). Right Panels. The putative LDPC markers epithelial cell adhesion molecule (EpCAM) and hepatocytes nuclear factor (HNF)-3 β were detected by immunoblot analysis.

As illustrated in FIG. 8, cells that were cultured in the presence of PEDF or 44-mer PEDF emitted autofluorescence under fluorescence microscope, whereas cells cultured in the presence of 34-mer PEDF emitted very little autofluorescence or none at all. Similarly, the expression of the two LDPC markers, EpCAM and HNF3-βconfirmed the LDPCs exhibits self-renewal property when treated by PEDF or 44-mer PEDF.

Figure 9:
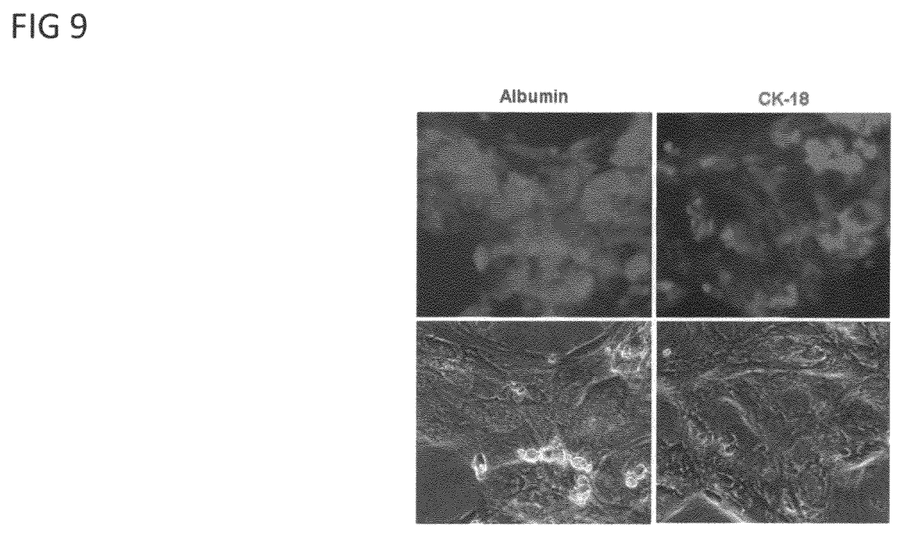
FIG. 9 are phase-contrast and immunofluorescence photographs that illustrate PEDF and 44-mer PEDF—expanded LDPCs retain the ability of differentiating into hepatocyte demonstrated by cells staining for albumin and CK-18 in accordance with one embodiment of this invention.

The cultured LDPCs were further tested for their ability to differentiate into hepatocytes by measuring the well-known hepatocyte markers, albumin and cytokeratin (CK)-18, under immunofluorescence microscope (FIG. 9), with albumin and CK-19 emitting green and red fluorescence, respectively. The finding confirmed that the cultured LDPCs still possess their ability to differentiate.

In sum, results from example 2.1 confirms that 34-mer PEDF functions similarly to PEDF by inactivating HSCs; and results from examples 2.2 and 2.3 confirm that 44-mer PEDF functions similarly to PEDF by enhancing the self-renewal activity of LDPCs; hence 34-mer PEDF or 44-mer PEDF may be used independently or concomitantly as an agent for treating or ameliorating liver cirrhosis.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating liver cirrhosis in a mammalian subject comprising administering to the subject in need thereof a polypeptide having 34 amino acid residues in length and the amino acid sequence of SEQ ID NO: 1, wherein the polypeptide is capable of inactivating hepatic stellate cells (HSCs).

2. The method of claim 1, wherein the polypeptide is administered parenterally every 1 to 10 days with a dose of 0.25 to 2.5 µg polypeptide/Kg of body weight.

3. The method of claim 1, wherein the mammalian subject is human.

4. The method of claim 1, wherein the inactivation of HSCs is characterized by having diminished level of α-smooth muscle actin (α-SMC), collagen type I and monocyte chemoattractant protein-1 (MCP-1) as compared with that of the control.

5. A method of treating liver cirrhosis in a mammalian subject comprising administering to the subject in need thereof a polypeptide having 44 amino acid residues in length and the amino acid sequence of SEQ ID NO: 2, wherein the polypeptide is capable of enhancing the replication of liver-derived progenitor cells (LDPCs).

6. The method of claim 5, wherein the polypeptide is administered parenterally every 1 to 10 days with a dose of 0.25 to 2.5 µg polypeptide/Kg of body weight.

7. The method of claim 5, wherein the mammalian subject is human.

* * * * *

SEQUENCE LISTING

```
<160> NUMBER OF SEQ ID NOS: 8

<210> SEQ ID NO 1
<211> LENGTH: 34
<212> TYPE: PRT
<213> ORGANISM: artificial sequence
<220> FEATURE:
<223> OTHER INFORMATION: synthetic peptide

<400> SEQUENCE: 1

Asp Pro Phe Phe Lys Val Pro Val Asn Lys Leu Ala Ala Ala Val Ser
1               5                   10                  15

Asn Phe Gly Tyr Asp Leu Tyr Arg Val Arg Ser Ser Thr Ser Pro Thr
            20                  25                  30

Thr Asn

<210> SEQ ID NO 2
<211> LENGTH: 44
<212> TYPE: PRT
<213> ORGANISM: artificial sequence
<220> FEATURE:
<223> OTHER INFORMATION: synthetic peptide

<400> SEQUENCE: 2

Val Leu Leu Ser Pro Leu Ser Val Ala Thr Ala Leu Ser Ala Leu Ser
```

```
1               5                  10                 15
Leu Gly Ala Glu Gln Arg Thr Glu Ser Ile Ile His Arg Ala Leu Thr
            20                  25                  30

Thr Asp Leu Ile Ser Ser Pro Asp Ile His Gly Thr
        35                  40
```

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
cctctgttac tgcccctgag                                          20

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
gcctgcaccc agttgttaat                                          20

<210> SEQ ID NO 5
<211> LENGTH: 20
<212> TYPE: DNA
<213> ORGANISM: artificial sequence
<220> FEATURE:
<223> OTHER INFORMATION: primer

<400> SEQUENCE: 5
ccctggcaaa gcatttgtat                                          20

<210> SEQ ID NO 6
<211> LENGTH: 20
<212> TYPE: DNA
<213> ORGANISM: artificial sequence
<220> FEATURE:
<223> OTHER INFORMATION: primer

<400> SEQUENCE: 6
actggcaccc ttgaaaaatg                                          20

<210> SEQ ID NO 7
<211> LENGTH: 21
<212> TYPE: DNA
<213> ORGANISM: artificial sequence
<220> FEATURE:
<223> OTHER INFORMATION: interference RNA

<400> SEQUENCE: 7
caccauuugu caucuacgat t                                        21

<210> SEQ ID NO 8
<211> LENGTH: 21
<212> TYPE: DNA
<213> ORGANISM: artificial sequence
<220> FEATURE:
<223> OTHER INFORMATION: interference RNA

<400> SEQUENCE: 8
ucguagauga caaauggugt t                                        21